United States Patent [19]

Smith

[11] 4,151,184

[45] Apr. 24, 1979

[54] 2,2-DIFLUORO-13,14-DIDEHYDRO-PGE$_1$ COMPOUNDS

[75] Inventor: Herman W. Smith, Kalamazoo, Mich.

[73] Assignee: The Upjohn Company, Kalamazoo, Mich.

[21] Appl. No.: 775,075

[22] Filed: Mar. 7, 1977

Related U.S. Application Data

[62] Division of Ser. No. 657,739, Feb. 13, 1976, Pat. No. 4,029,681.

[51] Int. Cl.$^2$ ............................................. C07C 177/00
[52] U.S. Cl. ................................... 260/408; 560/121; 562/503
[58] Field of Search ............................ 260/514 D, 408; 560/121; 562/503

[56] References Cited

U.S. PATENT DOCUMENTS

| | | | |
|---|---|---|---|
| 3,914,282 | 10/1975 | Pike | 260/468 |
| 3,931,411 | 1/1976 | Potts | 424/312 |
| 3,932,463 | 1/1976 | Schaub et al. | 260/340.7 |
| 3,933,889 | 1/1976 | Maserlin | 260/468 |
| 3,933,899 | 1/1976 | Nelson | 260/473 |
| 3,959,346 | 5/1976 | Schneider | 260/468 |
| 3,962,293 | 6/1976 | Magerlin | 260/408 |

OTHER PUBLICATIONS

Pappo et al., Tet. Letters, 2627 (1972).
Burger, Medicinal Chemistry, pp. 81, 82 (1960).

*Primary Examiner*—Robert Gerstl
*Attorney, Agent, or Firm*—Robert A. Armitage

[57] ABSTRACT

This invention comprises certain analogs of the prostaglandins in which the double bond between C-13 and C-14 is replaced by a triple bond. A so provided in this invention, are novel chemical processes and novel chemical intermediates useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

51 Claims, No Drawings

2,2-DIFLUORO-13,14-DIDEHYDRO-PGE₁ COMPOUNDS

The present application is a divisional application of Ser. No. 657,739, filed Feb. 13, 1976, now issued as U.S. Pat. No. 4,029,681 on June 14, 1977.

The present invention relates to prostaglandin analogs for which the essential material constituting a disclosure therefor is incorporated by reference here from U.S. Pat. No. 4,029,681, issued June 14, 1977.

I claim:

1. A prostaglandin analog of the formula:

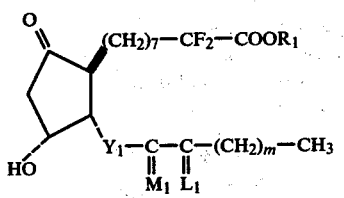

wherein $Y_1$ is —C≡C—;
wherein m is one to 5, inclusive;
wherein $M_1$ is

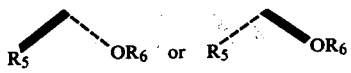

wherein $R_5$ and $R_6$ are hydrogen or methyl, with the proviso that one of $R_5$ and $R_6$ is methyl only when the other is hydrogen;
wherein $L_1$ is

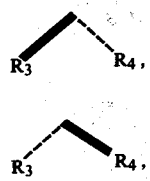

or a mixture of

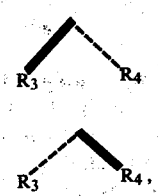

wherein $R_3$ and $R_4$ are hydrogen, methyl, or fluoro, being the same or different, with the proviso that one of $R_3$ and $R_4$ is fluoro only when the other is hydrogen or fluoro;
wherein $R_1$ is hydrogen, alkyl of one to 12 carbon atoms, inclusive, cycloalkyl of 3 to 10 carbon atoms, inclusive aralkyl of 7 to 12 carbon atoms, inclusive, phenyl, phenyl substituted with one, two, or three chloro or alkyl of one to 3 carbon atoms, inclusive, or a pharmacologically acceptable cation.

2. A prostaglandin analog of the formula

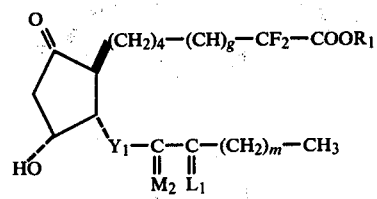

wherein $Y_1$ is —C≡C—;
wherein g is one, two, or 3;
wherein m is one to 5, inclusive;
wherein $M_1$ is

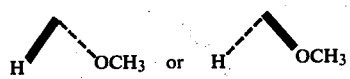

wherein $L_1$ is

or a mixture of

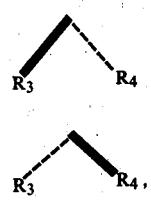

wherein $R_3$ and $R_4$ are hydrogen, methyl, or fluoro, being the same or different, with the proviso that one of $R_3$ and $R_4$ is fluoro only when the other is hydrogen or fluoro;
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

3. 2,2-Difluoro-13,14-didehydro-8β, 12α-PGE₁, 15-methyl ether, a compound according to claim 2.

4. 2,2-Difluoro-13,14-didehydro-8β, 12α-PGE₁, methyl ester, 15-methyl ether, a compound according to claim 2.

5. A prostaglandin analog of the formula:

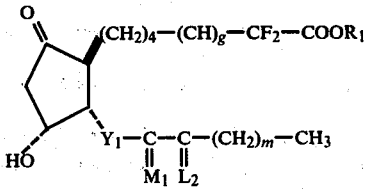

wherein $Y_1$ is —C≡C—;
wherein g is one, two, or 3;
wherein m is one to 5, inclusive;
wherein $M_1$ is

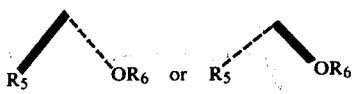

wherein $L_2$ is

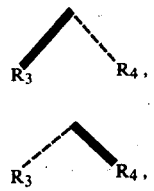

or a mixture of

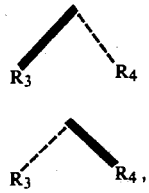

wherein one of $R_3$ and $R_4$ are methyl or fluoro and the other is hydrogen, methyl or fluoro, with the proviso that one of $R_3$ and $R_4$ is fluoro only when the other is hydrogen or fluoro;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl subsituted with one, two, or three chloro or alkyl of one to 3 carbon atoms, inclusive, or a pharmacologically acceptable cation.

6. A compound according to claim 5, wherein at least one of $R_3$ and $R_4$ is methyl.

7. A compound according to claim 6, wherein $R_3$ and $R_4$ are both methyl.

8. A compound according to claim 7, wherein $R_5$ is methyl.

9. 2,2-Difluoro-15,16,16-trimethyl-13,14-didehydro-8β, 12α-PGE$_1$, methyl ester, a compound according to claim 8.

10. A compound according to claim 7, wherein $R_6$ is methyl.

11. 2,2-Difluoro-16,16-dimethyl-13,14-didehydro-8β, 12α-PGE$_1$, methyl ester, 15-methyl ether, a compound according to claim 10.

12. A compound according to claim 7, wherein $R_5$ and $R_6$ are both hydrogen.

13. 2,2-Difluoro-16,16-dimethyl-13,14-didehydro-8β, 12α-PGE$_1$, a compound according to claim 12.

14. 2,2-Difluoro-16,16-dimethyl-13,14-didehydro-8β, 12α-PGE$_1$, methyl ester, a compound according to claim 12.

15. A compound according to claim 5, wherein at least one of $R_3$ and $R_4$ is fluoro.

16. A compound according to claim 15, wherein $R_3$ and $R_4$ are both fluoro.

17. A compound according to claim 16, wherein $R_5$ is methyl.

18. 2,2-Difluoro-15-methyl-16,16-difluoro-13,14-didehydro-8β, 12α-PGE$_1$, methyl ester, a compound according to claim 17.

19. A compound according to claim 16, wherein $R_6$ is methyl.

20. 2,2-Difluoro-16,16-difluoro-13,14-didehydro-8β, 12α-PGE$_1$, methyl ester, 15-methyl ether, a compound according to claim 19.

21. A compound according to claim 16, wherein $R_5$ and $R_6$ are both hydrogen.

22. 2,2,16,16-Tetrafluoro-13,14-didehydro-8β, 12α-PGE$_1$, a compound according to claim 21.

23. 2,2,16,16-Tetrafluoro-13,14-didehydro-8β, 12α-PGE$_1$, methyl ester, a compound according to claim 21.

24. A prostaglandin analog of the formula:

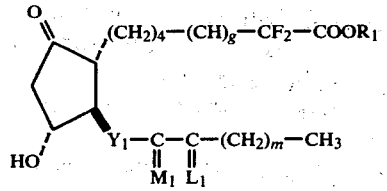

wherein $Y_1$ is —C≡C—;
wherein g is one, two, or 3;
wherein m is one to 5, inclusive;
wherein $M_1$ is

wherein $R_5$ is hydrogen and $R_6$ is hydrogen or methyl,
wherein $L_1$ is

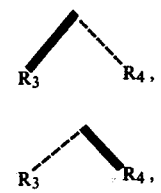

or a mixture of

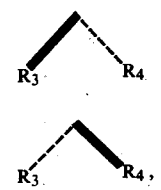

wherein $R_3$ and $R_4$ are hydrogen, methyl, or fluoro, being the same or different, with the proviso that one of $R_3$ and $R_4$ is fluoro only when the other is hydrogen or fluoro;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

25. A compound according to claim 24, wherein g is three.

26. A compound according to claim 24, wherein g is one.

27. A compound according to claim 26, wherein $R_3$ and $R_4$ are both hydrogen.

28. A compound according to claim 27, wherein $R_6$ is methyl.

29. 2,2-Difluoro-13,14-didehydro-PGE$_1$, 15-methyl ether, a compound according to claim 28.

30. 2,2-Difluoro-13,14-didehydro-PGE$_1$, methyl ester, 15-methyl ether, a compound according to claim 28.

31. A compound according to claim 27, wherein $R_5$ and $R_6$ are both hydrogen.

32. 2,2-Difluoro-13,14-didehydro-$PGE_1$, a compound according to claim 31.

33. 2,2-Difluoro-13,14-didehydro-$PGE_1$, methyl ester, a compound according to claim 31.

34. A compound according to claim 26, wherein at least one of $R_3$ and $R_4$ is methyl.

35. A compound according to claim 34, wherein $R_3$ and $R_4$ are both methyl.

36. A compound according to claim 35, wherein $R_5$ is methyl.

37. 2,2-Difluoro-15,16,16-trimethyl-13,14-didehydro-$PGE_1$, methyl ester, a compound according to claim 36.

38. A compound according to claim 35, wherein $R_6$ is methyl.

39. 2,2-Difluoro-16,16-dimethyl-13,14-didehydro-$PGE_1$, methyl ester, 15-methyl ether, a compound according to claim 38.

40. A compound according to claim 35, wherein $R_5$ and $R_6$ are both hydrogen.

41. 2,2-Difluoro-16,16-dimethyl-13,14-didehydro-$PGE_1$, a compound according to claim 40.

42. 2,2-Difluoro-16,16-dimethyl-13,14-didehydro-$PGE_1$, methyl ester, a compound according to claim 40.

43. A compound according to claim 26, wherein at least one of $R_3$ and $R_4$ is fluoro.

44. A compound according to claim 43, wherein $R_3$ and $R_4$ are both fluoro.

45. A compound according to claim 44, wherein $R_5$ is methyl.

46. 2,2-Difluoro-15-methyl-16,16-difluoro-13,14-didehydro-$PGE_1$, methyl ester, a compound according to claim 45.

47. A compound according to claim 44, wherein $R_6$ is methyl.

48. 2,2,16,16-Tetrafluoro-13,14-didehydro-$PGE_1$, methyl ester, 15-methyl ether, a compound according to claim 47.

49. A compound according to claim 44, wherein $R_5$ and $R_6$ are both hydrogen.

50. 2,2,16,16-Tetrafluoro-13,14-didehydro-$PGE_1$, a compound according to claim 49.

51. 2,2,16,16-Tetrafluoro-13,14-didehydro-$PGE_1$, methyl ester, a compound according to claim 49.

* * * * *